(12) United States Patent
Liu et al.

(10) Patent No.: US 7,851,616 B2
(45) Date of Patent: Dec. 14, 2010

(54) DEVELOPMENT OF ASTHMA THERAPY WITH RAAV-MEDIATED AMCASE SHRNA

(75) Inventors: Chao-Lin Liu, Taipei (TW); Ching-Jen Yang, Zhongli (TW); Chia-Rui Shen, Gueishan Township, Taoyuan County (TW)

(73) Assignee: MingChi University of Technology, Taipei Hsien (TW)

( * ) Notice: Subject to any disclaimer, the term of this patent is extended or adjusted under 35 U.S.C. 154(b) by 0 days.

(21) Appl. No.: 12/328,095

(22) Filed: Dec. 4, 2008

(65) Prior Publication Data

US 2010/0143450 A1 Jun. 10, 2010

(51) Int. Cl.
*C07H 21/02* (2006.01)
*C07H 21/04* (2006.01)

(52) U.S. Cl. .................. 536/24.5; 536/23.1; 536/24.3; 536/24.33

(58) Field of Classification Search ................. 536/24.5
See application file for complete search history.

(56) References Cited

U.S. PATENT DOCUMENTS

| | | | | |
|---|---|---|---|---|
| 7,214,373 | B2 * | 5/2007 | Elias et al. | 424/139.1 |
| 2005/0214297 | A1 * | 9/2005 | Mao et al. | 424/145.1 |

OTHER PUBLICATIONS

Scanlon, KJ (Current Pharmaceutical Biotechnology, 2004 vol. 5:415-420).*

* cited by examiner

*Primary Examiner*—Sean McGarry
*Assistant Examiner*—Terra Cotta Gibbs
(74) *Attorney, Agent, or Firm*—The Weintraub Group, P.L.C.

(57) ABSTRACT

The invention provides small interfering RNA (siRNA) and their carriers that could treat asthma in mammalian through inhibiting acidic mammalian chitinase (AMCase) gene expression. The invention further provides a composition comprising siRNA of the present invention and a carrier. The invention also provides a method for treating asthma of a subject.

5 Claims, 8 Drawing Sheets

DEVELOPMENT OF ASTHMA THERAPY WITH RAAV-MEDIATED AMCASE SHRNA

FIELD OF THE INVENTION

The present invention relates to methods and molecules for treating asthma. The present invention provides short nucleotide sequences and vectors comprising these sequences that can inhibit AMCase (acidic mammalian chitinase) expression in mammalian.

BACKGROUND OF THE INVENTION

Asthma has become a serious public health issue worldwide, and its prevalence has doubled in numerous industrialized countries (Beasley et al., J Allergy Clin Immunol 2000; 105, S466-472). Chronic airway inflammation characterized by pathological immune response is considered the hallmark of asthma. The key features of asthma include the production of allergen-specific IgE, resulting in immediate-type hypersensitivity reactions followed by the development of late phase responses such as eosinophil recruitment, mucus production, and airway hyperresponsiveness (AHR). In addition, eosinophilic inflammation driven by Th2-cytokines (including IL-4, IL-5 and IL-13) is deemed to play a crucial role in the pathogenesis of asthma (Renauld et al., J Clin Pathol 2001; 481:54, 577-589; Hoshino et al., Int Immunol 2004; 16, 1497-1505). Particularly, several studies have highlighted the crucial contribution of IL-13 in promoting the development of asthmatic features.

Acidic mammalian chitinase (AMCase), the prototypic chitinase, has been found to be induced during Th2-mediated inflammation through an IL-13-dependent mechanism (Kawada et al., Keio J Med 2007; 56, 21-27). It is a 50-kDa protein, containing a 39-kDa N-terminal catalytic domain that hydrolyzed chitin, a hinge region, and a C-terminal chitin-binding domain. AMCase is highly expressed in the lungs of asthmatic patients, as well as in mice models of asthma (Ramanathan et al., Am J Rhinol 2006; 20:479, 330-335). In fact, the hyper-expression of AMCase has also been found in the other airway tissues including the alveolar macrophages and lung epithelial cells in OVA-stimulated mice (Zhu et al., Science 2004; 304, 1678-1682). Inhibition of AMCase activity with specific antibodies appeared to be able to reduce the inflammatory response in BALF and lung tissues. However, neutralization of AMCase activity does not directly affect the expression of IL-4 and IL-13 (Zhu et al., Science 2004; 304, 1678-1682). It was found that AMCase could modulate the expression of several proinflammatory chemokines-including macrophage inflammatory protein (MIP)-1β, macrophage chemoattractant protein (MCP)-1 and eotaxin that play a crucial role in Th2-mediated airway inflammation (Mori, et al. Int Arch Allergy Immunol 2006; 140 Suppl 1, 55-58).

RNA interference (Fire, et al. Nature 1998; 391, 806-811) has become a powerful tool in downregulation of gene expression in mammalian cells and animal models (Cullen, et al. Gene Ther 2004; 13, 503-508). Recent studies have shown that short interfering (21-25 bp) RNA molecules (siRNA—small interfering RNA), but not long dsRNA (greater than 30 bp), are key elements of RNAi and appear to inhibit gene expression. Short hairpin RNA (shRNA) has been shown to be efficiently processed into siRNA inside the cells. In the last few years, some methods for expressing siRNAs in cells have been developed based on transcription of short hairpin RNAs (shRNAs) by RNA polymerase III promoter (Sui et al., Proc Natl Acad Sci USA 2002; 99, 5515-5520), such as U6 and H1.

Delivery of siRNA into mammalian cells has been achieved via liposome, polymer and viral vectors. (Moore et al., J Gene Med 2005; 7, 918-925; Urban-Klein et al., Gene Ther 2005; 12, 461-466; Xu et al., Mol Ther 2005; 11, 523-530; Li et al., Cell Cycle; 5, 2103-2109; Aigner et al., Curr Opin Mol Ther 2007; 9, 345-352). Viral vectors appear to have the highest delivery efficiency. A serious problem with viral vectors is their immunogenity. In this regard, repeated applications may result in the production of neutralizing antibodies by the host. To overcome this issue, the use of adeno-associated virus (AAV), which promotes longterm transgene expression, has been proposed. AAV vector offers a compromise between an adequate level of transduction and an acceptable safety profile (Leung et al., J Gene Med 2007; 9, 10-21). Hence, several reports have successfully used AAV-mediated shRNA therapeutic system in controlling viral infections (Ge et al., Proc Natl Acad Sci USA 2004; 101, 8676-8681) and genetic disorders Rodriguez-Lebron et al., Mol Ther 2005; 12, 618-633). In the present study, we demonstrated that specific suppression of elevated AMCase results in a reduced eosinophilic and Th2-mediated airway inflammation in a mouse model of asthma. We also investigated whether the inhibition of AMCase may be associated with a reduced expression of IL-13, eotaxin, and other proinflammatory molecules.

SUMMARY OF THE INVENTION

Figure 1A:
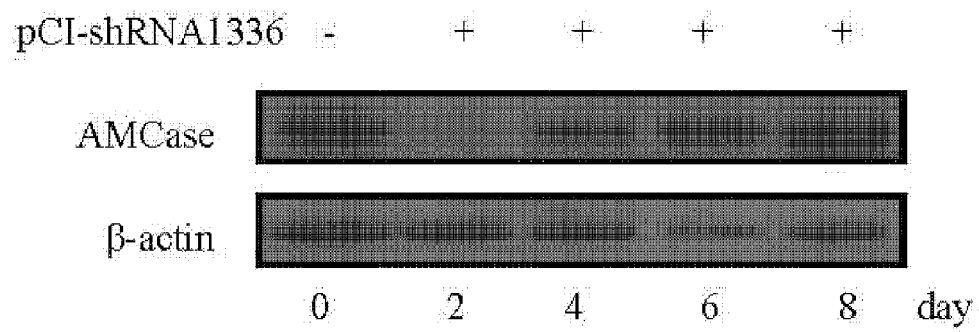
FIG. 1. Inhibitory effects of pCI-shRNA and rAAV-mediated shRNA on AMCase expression. (a). Representative Western blot of an AMCase-overexpres sing stable cell line treated by pCI-shRNA 1336 for 48 hours. (b). AMCase expression of the same cell line following infection with rAAV vector expressing shRNA1336, and harvested on days 0, 2, 4, 6, and 8. Western blots using anti-AMCase and anti-actin antibodies are shown.

The invention includes the small interfering RNA polynucleotide that could treat asthma and the vectors comprising them, which also include the method of administrating the vector to a subject.

An isolated small interfering RNA (siRNA) polynucleotide, comprising at least one polynucleotide that is selected from the group consisting of (i) a polynucleotide having the nucleotide sequence set forth in SEQ ID NO: 1 or (ii) a polynucleotide having the nucleotide sequence set forth in SEQ ID NO: 2 or (iii) a polynucleotide having the nucleotide sequence set forth in SEQ ID NO: 3.

A composition comprising: an siRNA or a small hairpin RNA or short hairpin RNA (shRNA) targeted to a target transcript, or a nucleic acid that comprises a template for transcription of one or more RNA molecules that hybridize or self-hybridize to form an siRNA or shRNA targeted to a target transcript, wherein the target transcript encodes a protein named acidic mammalian chitinase (AMCase) involved in airway hyper responsiveness and inflammation in mammalian.

A method for treating asthma of a subject, comprising steps of: administrating the subject with a therapeutically composition which is a pharmaceutical acceptable carrier of aforementioned; and the way to administrate the subject with the therapeutically composition is through inhalation.

DETAILED DESCRIPTION OF THE INVENTION

The potential therapeutic applications of RNAi technology to down regulate gene expression have been widely evaluated. Unfortunately, only a few reports have focused on RNAi-based treatment for asthma (Lee et al., Mol Ther 2008; 16, 60-444 65; Lively et al., J Allergy Clin Immunol 2008; 121, 88-94.), an emergent worldwide health issue (Beasley et al., J Allergy Clin Immunol 2000; 105, S466-472). In the present study, we have shown that AMCase expression can be effectively down regulated by means of rAAV-mediated shRNA. Reduction of AMCase expression resulted in an improvement of the asthmatic inflammatory response in OVA-sensitized asthmatic mice. Altogether, these findings suggest the potential usefulness of RNA interference targeting AMCase as a novel therapeutic strategy in asthma. This possibility is in keeping with previous findings showing that AMCase may play a key role in IL-13-mediated responses occurring in asthma. (Zhu et al., Science 2004; 304, 1678-1682).

Cytokines are known to play an important role in asthma, including pulmonary eosinophilia, serum IgE elevation, and excessive mucus production (Wills-Karp and Karp, N Engl J Med 2004; 351, 1455-1457). In this study we have shown that rAAV-shRNA-treated mice showed a significantly reduced IL-13 expression in their BALF (bronchoalveolar lavage fluid). This reduction was directly correlated to AMCase inhibition in BALF cells. In contrast, only a minor effect on IL-4 and IL-5 expression was seen in lung tissues. Notably, rAAV-shRNA suppressed the induction of AMCase expression by IL-13 in mouse lung epithelial cells. In this regard, Zhu et al. have previously shown a significant hyper-expression of AMCase in IL-13 transgenic mice (Zhu et al., Science 2004; 304, 1678-1682). On the other hand, IL-13-null mice failed to express AMCase following an allergen challenge (Zhu et al., Science 2004; 304, 1678-1682). These findings highlight the inter-independence between IL-13 and AMCase in the pathogenesis of asthmatic inflammation. It has been also previously suggested that AMCase could regulate the expression of several chemokines (eotaxin, MCP-1 and MIP-1$\beta$) in asthma. (Zhu et al., Science 2004; 304, 1678-1682) Eotaxin is a chemo attractant for eosinophils in the lung following an allergen challenge (Conroy and Williams, Respir Res 2001; 2, 150-156; Zimmermann et al., J Allergy Clin Immunol 2003; 111, 227-242), but the exact relationship between AMCase expression and eotaxin remains unclear. MCP-1 and MIP-1$\beta$ are thought to play a role in the airway inflammation. Accordingly, several reports have shown elevated levels of MCP-1 and MIP-1$\beta$ in asthmatic subjects. (Zhu et al., Science 2004; 304, 1678-1682). In the present invention, inhibition of AMCase in OVA asthmatic mice led to a reduction in eotaxin expression in their BALF. This result is keeping with the low number of eosinophils detected in BALF. Moreover, expression of eotaxin, MCP-1 and MIP-1$\beta$ was also remarkably reduced after treatment with AAV-shRNA.

To overcome poor siRNA transfection rates in vivo, we used the AAV vector as a delivery tool for shRNA in keeping with similar studies on bronchial diseases (Zavorotinskaya et al., Mol Ther 2003; 7, 155-162; Flotte, Curr Gene Ther 2005; 5, 361-366; Leung et al., J Gene Med 2007; 9, 10-21). Murphy and coworkers have previously compared the efficacy of a single intramuscular injection versus intratracheal administration of a rAAV vector carrying the IL-4 receptor antagonist in OVA-sensitized mice. The authors showed that intratracheal administration resulted in significant local effects in the airways, with no systemic or local adverse effects (Zavorotinskaya et al., Mol Ther 2003; 7, 155-162). Accordingly, the AAV vector achieved a better transfection rate not only in vivo, but also in vitro. In the present study, a liposome-based transfection with pCI-shRNA resulted in an AMCase inhibition of approximately 85%, whereas suppression rate of almost 100% was achieved by rAAV-shRNA. These data clearly indicate that rAAV may be regarded as an optimal transfection vector.

Example 1

Reduction of AMCase Expression Levels by Hairpin-Type siRNA

The example expresses the effect of reducing AMCase expression levels by hairpin-type siRNA and rAAV mediated shRNA1336. The siRNA nucleotide sequences specific for AMCase were selected from three candidates.

Three sequences specifically targeting murine AMCase were designed as siRNA185 (SEQ ID NO: 1), siRNA897 (SEQ ID NO:2) and siRNA1336 (SEQ ID NO:3), shRNA molecules with the same sequences as siRNA, but containing an 8 random nucleotides (CAAGCTTC) loop structure and a 3' TTTT terminator nucleotides overhanging at 3'-end were inserted into a pCI-neo plasmid vector with a mU6 promoter.

These three hairpin-type siRNA expression vector containing the mouse U6 promoter were constructed (pCI-shRNA185, pCI-shRNA897 and pCI-shRNA1336). Their ability to suppress AMCase expression was tested in stable cell lines overexpressing AMCase.

The AMCase overexpressing cell line was set up by the following steps: RNA was extracted from mouse lung tissues using the TriZol reagent (Invitrogen) and reversely transcribed (RT) with a two-step RT-polymerase chain reaction (PCR) kit (Invitrogen). The full length AMCase sequence was amplified with the following primers: forward 5'-ATC AGAATTCTAT GGC CAA GCT ACT TCTC-3' (SEQ ID NO: 4), and reverse 5'-TTT CTG CGG CCGCAT GGC ATT AGG TTC ATG GC-3' (SEQ ID NO:5). The AMCase overexpressing cell line was established by transfection to 3T3 cells of a pTriEx-neo vector containing the AMCase sequence. A dilution series under G418 selection pressure was applied.

The three shRNA constructs were packed by Lipofetamine 2000 and send to AMCase overexpressing cells. All three constructs were able to reduce AMCase expression at different extents. Specifically, AMCase expression was reduced by 85% with shRNA1336, by 50% with shRNA185 and by 20% with shRNA 897 (FIG. 1a).

Example 2

Reduction of AMCase Expression Levels by rAAV Mediated shRNA1336

Secondly, AAV vectors encoding GFP and shRNA1336, rAAV-GFP, and rAAV-shRNA1336 were cloned and tested for their inhibitory effects on AMCase expression.

The shRNA1336 was subcloned into an adeno-associated virus vector pAAV2-IRES-GFP. Virus production was performed with the AAV2 helper system (Stratagene). Briefly, plasmid DNA (rAAV-shRNA1336-IRES-GFP plasmid plus the pRC vector encoding Rep and Cap proteins and the pHelper vector encoding adenovirus gene products) was used to transfect 293T cells at an 80% confluence stage. Cell lysates were collected 48 hours post-transfection and purified by CsCI density gradient centrifugation. Titers of rAAV-shRNA1336-IRES-GFP were determined using RT-PCR analysis by calculating the viral genome copy number. Expression of GFP and actin were analyzed by real-time PCR using a Light-Cycler PCR system (Roche). Actin 300 was used as a housekeeping gene, and its' forward primer: 5'-GAAACTACATTCAATTCCATC-3' (SEQ ID NO: 6); reverse primer: 5'-CTAGAAGCACTTGCGGTGCAC-3' (SEQ ID NO: 7).

The reaction parameters for actin 300 and GFP amplification (forward primer: 5'-ATGGTGAGCAAGCAGATCCTG-3'(SEQ ID NO:8); reverse primer: 5'-GGTGCGCTCGTA-CACGAAGCC-3' (SEQ ID NO:9)) were as follows: initial denaturation at 95° C. for 10 min, followed by 35 cycles at 95° C. for 10 s, 50° C. for 10 s, and 72° C. for 10 s.

Figure 1B:
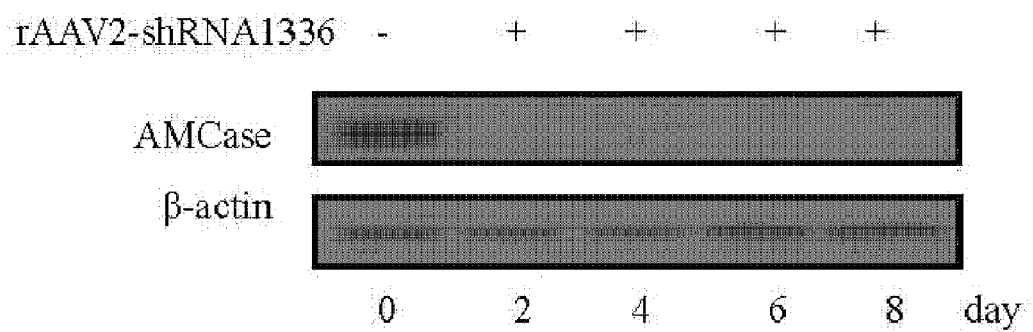

Infection with rAAV-shRNA1336 significantly suppressed AMCase expression in the stable cell line between days 2 and 8 (FIG. 1b). Altogether, these findings indicate that rAAV-shRNA1336 showed the better long-term effect on the reduction of AMCase expression.

Example 3

Develop an OVA (Ovalbumin) Sensitized Mice

Pathogen-free wild type female BALB/C mice from the National Laboratory Animal Centre (Taipei, Taiwan, ROC) were used in this study. Mice were 6-8 weeks old at the beginning of the experiment. Animals were maintained and handled according to the guidelines of Animal Care Committee of Chang Gung University and the NIH Guidelines for the Care and Use of Laboratory Animals. Mice were injected intraperitoneally with either chicken OVA (20 μg) complexed with alum or normal saline alone. The procedure was repeated 3 days thereafter. Thirteen days after the first immunization, animals were re-injected intraperitoneally with chicken OVA. Moreover, mice received by inhalation either an aerosol of OVA (2%, w/v) in normal saline or normal saline solution alone. Mice were thereafter challenged with OVA for four times on days 16, 20, 23, and 27. On day 25, $1.0 \times 10^{11}$ genome copies of rAAV-shRNA1336-IRES-GFP, rAAV-IRES-GFP or normal saline solution were administered intratracheally. Mice were sacrificed on day 28.

On day 28, 24 hr after the last challenge, the mice airway responsiveness was measured by whole body plethysmography (Buxco, Troy, N.Y.) (Lee et al., Mol Ther 2008; 16, 60-65). Briefly, mice were aerosolized normal saline or methacholine in increasing concentrations (0, 6.25, 12.5, 25, 50 mg/ml) for 3 minutes. Recordings were taken and averaged for 3 minutes after each nebulization. Airway reactivity was expressed as the mean Penh.

Example 4

Determination of OVA-Specific IgE in Mice Serum

Serum levels of OVA-specific IgE were measured by enzyme-linked immunosorbent assay (ELISA). Briefly, 96-well plates (Maxisorb, Nunc) were coated with OVA (10 Zg/ml) and blocked. After addition of serum samples at proper dilutions, biotin-conjugated rat-anti-mouse IgE was added to individual wells. The reaction was developed with Streptavidin-HRP. Substrate solution was then added to each well and the plates were incubated for 30 min at room temperature in a dark room. After addition of a stop solution, the absorbance was read with an ELISA plate reader at 450 nm. IgE concentrations were determined using a commercial mouse IgE standard (BD Pharmingen).

Example 5

Levels of AMCase in BALF and Lungs of Ova-Sensitized Asthmatic Mice

Figure 2A:
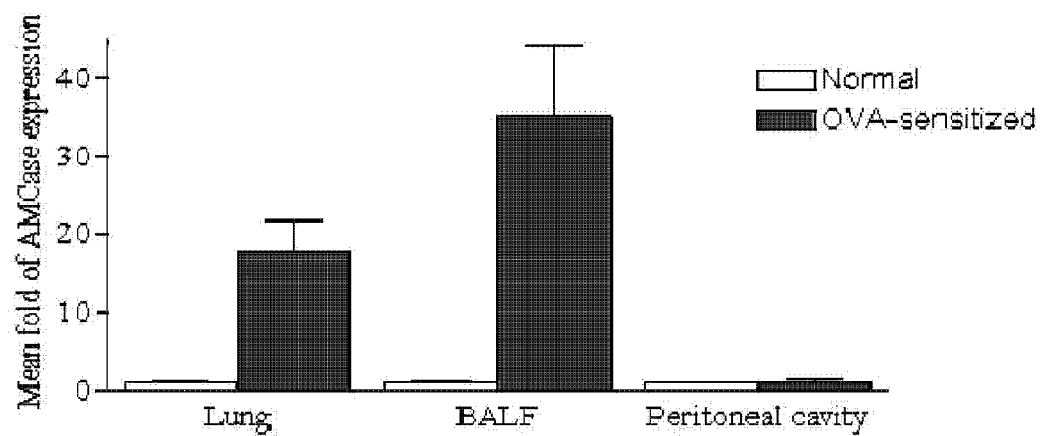
FIG. 2. AMCase expression quantified via (a) real-time PCR and (b) Western blot in normal saline controls (n=5) and OVA-sensitized mice (n=9). Cytology samples from lung tissues, BALF, and the peritoneal cavity were harvested. For panel (a), mRNA levels of AMCase expression detected by real-time RT-PCR were normalized to actin and compared with normal controls. For panel (b), AMCase protein levels were analyzed by Western blot ($*p<0.05$, nonparametric Mann-Whitney test).

To investigate whether elevated levels of AMCase expression are specifically located in the airway tissues of OVA-sensitized mice, the lung tissues, BALF, and peritoneal cells were harvested on day 28, 24 hours from the last OVA-challenge. Notably, a 17-fold and 37-fold increase in AMCase mRNA level was found in the lung tissues and BALF of OVA-sensitized mice, respectively. In contrast, no difference was found in peritoneal cells as compared with control experiments with normal saline (FIG. 2a). Similar findings were obtained when AMCase protein levels were measured.

Figure 2B:
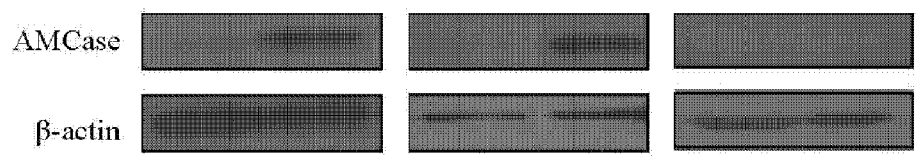

FIG. 2b shows significantly higher levels of AMCase only in lung tissue and BALF cells from OVA-sensitized mice. In peritoneal cells, such an increase was not found both at the mRNA and protein level. Thus, hyper expression of AMCase was limited to airway tissues of mice with allergic asthma.

Example 6

Figure 3A:
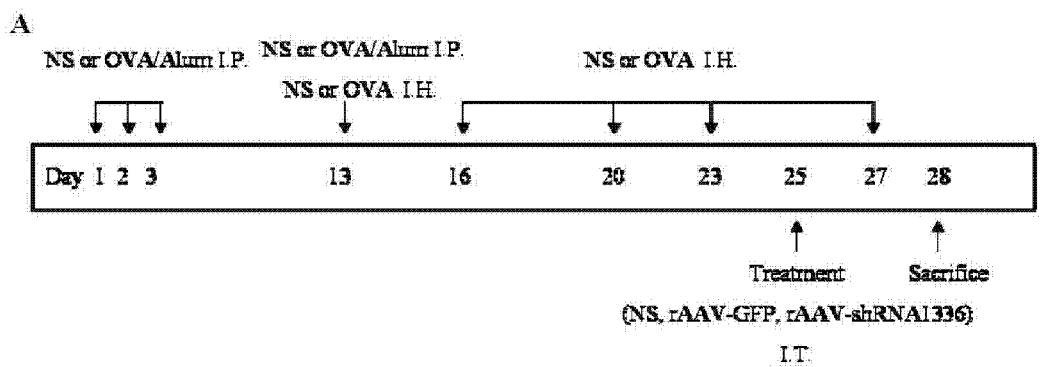
FIG. 3. Airway hyperrsponsiveness inhibited in rAAV-shRNA-treated mice. Panel (a), schematic protocol for rAAV treatment flowchart. Mice were sensitized and treated as described in the Methods. Panel (b), Airway hyperrsponsiveness was measured by whole body plethysmography. Data were expressed as Penh values. Normal saline controls (normal, n=4), sensitized mice (n=10), OVA sensitized mice receiving rAAV-GFP (n=4) and rAAV-shRNA1336 (n=7) ($*p<0.05$, nonparametric Mann-Whitney test). IH: inhalation; IP: intraperitoneal; IT: intratracheal.
Figure 3B:
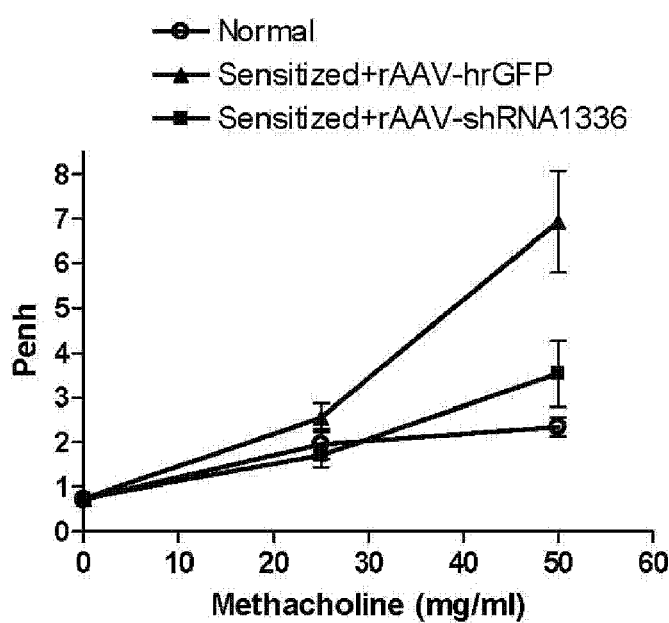
Figure 4A:
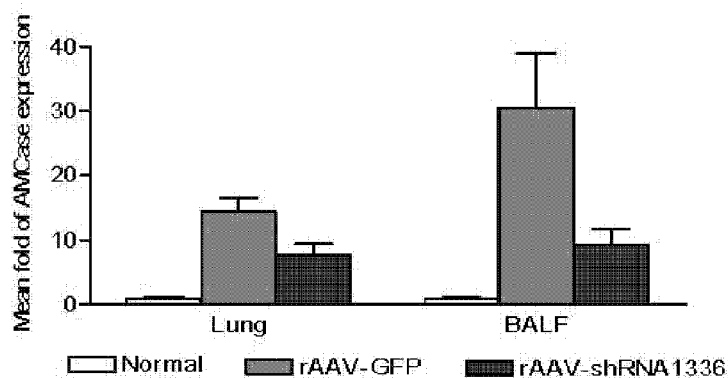
FIG. 4. Suppression of AMCase in lung tissues and BALF cells of rAAV-shRNA-treated mice. Panel (a), real-time PCR was performed to quantify AMCase mRNA in lung tissues and BALF cells. Data were normalized to actin and compared with normal controls. Panel (b), expression of AMCase in the lung as detected by IHC. Panel (c), AMCase activity in BALF cells measured by fluorogenic chitin substrate. Normal (normal, n=7), sensitized (n=7), rAAV-GFP (n=8) and rAAV-shRNA1336 (n=10) were investigated ($*p<0.05$, nonparametric Mann-Whitney test).
Figure 4B:
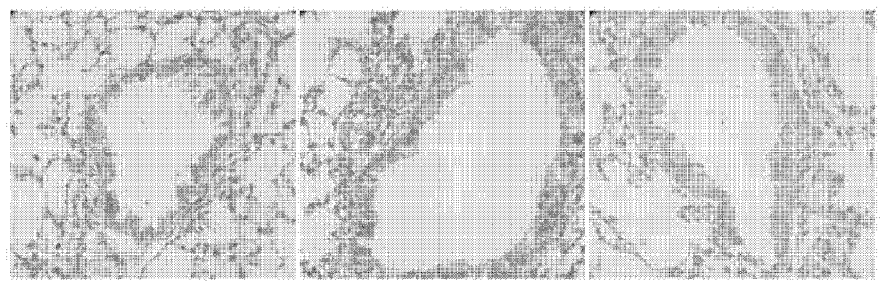
Figure 4C:
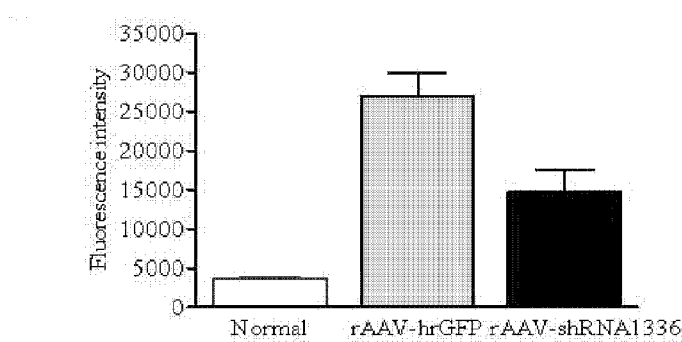

Reduction of AHR (Airway Hyper Responsiveness) and AMCase Expression in the Airways of OVA-Sensitized Mice Following rAAV-shRNA1336 Administration Since hyperexpression of AMCase was limited to airway tissues of mice with allergic asthma, we investigated whether rAAV-shRNA may prevent AMCase hyperexpression and allergic reactions. FIG. 3a depicted a schematic representation of the rAAV treatment protocols. After three days from intratracheal administration of 1011 rAAV encoding LacZ or GFP (rAAV-LacZ, rAAV-GFP), rAAV infection was evident in mice lung tissues and BALF cells. Mice were sacrificed for analysis on day 3 following rAAV infections. FIG. 3b showed that methacholine induced the significant increase of AHR in OVA-sensitized mice without further treatment or with rAAV-GFP. After the mice treating with rAAV-shRNA1336, their Penh values in responding to the induction of methacholine were dropped, similar to the ones of normal mice. FIG. 4a showed that AMCase expression was reduced by 2-fold in lungs and by 3-fold in BALF cells of mice treated with rAAV-shRNA1336 compared with mice receiving rAAV-GFP; however, both groups of OVA-sensitized mice showed relative higher levels of AMCase compared to normal saline experiments. AMCase protein levels or activity in lungs and BALF cells were also investigated by means of IHC or enzymatic assays using commercially fluorescence systems. FIG. 4b showed that AMCase was mainly expressed in the airway epithelial cells of OVA-sensitized animals receiving rAAV-GFP, while lower levels of AMCase expression were seen in rAAV-shRNA1336-treated animals. It is thus posited that a significant reduction in AMCase expression occurs following rAAV-shRNA infection. As it can be seen in FIG. 4c, AMCase activity was found to be inhibited in BALF cells of mice treated with rAAV-shRNA1336.

Example 7 rAAV-shRNA1336 Reduced Immunopathological Reactions in OVA Asthmatic Mice

Figure 5A:
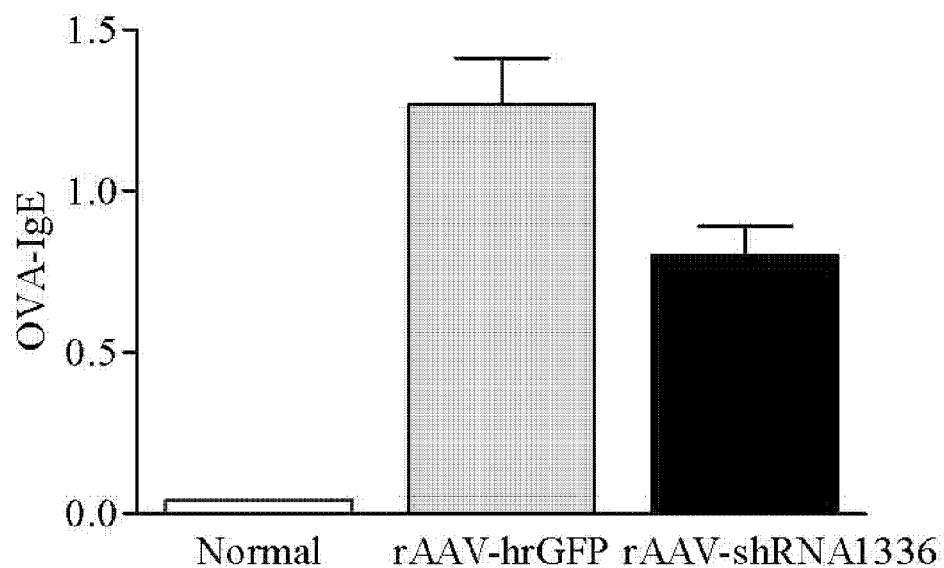
FIG. 5. Reduction of immunopathological responses in rAAV-shRNA-treated mice. Panel (a), serum levels of OVA-specific IgE were measured by ELISA. Panel (b), the number of eosinophils within BALF was calculated by microscopy at 400× magnification. Panel (c) H&E histopathology of the lung analyzed by microscopy at 100× and 400× magnifications. Normal (n=7), sensitized (n=7), rAAV-GFP (n=10) and rAAV-sh1336 (n=11) were investigated (*p<0.05, nonparametric Mann-Whitney test).
Figure 5B:
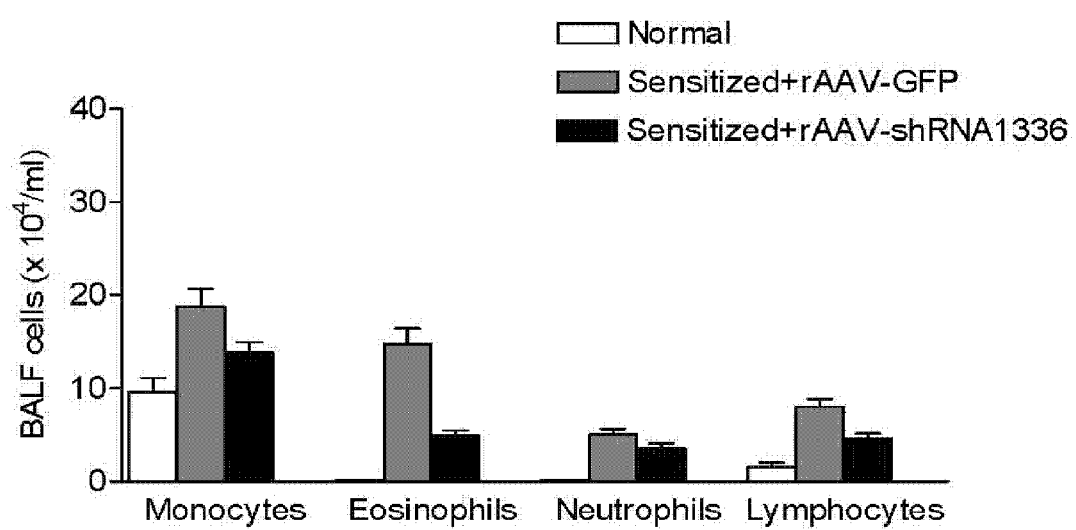
Figure 5C:
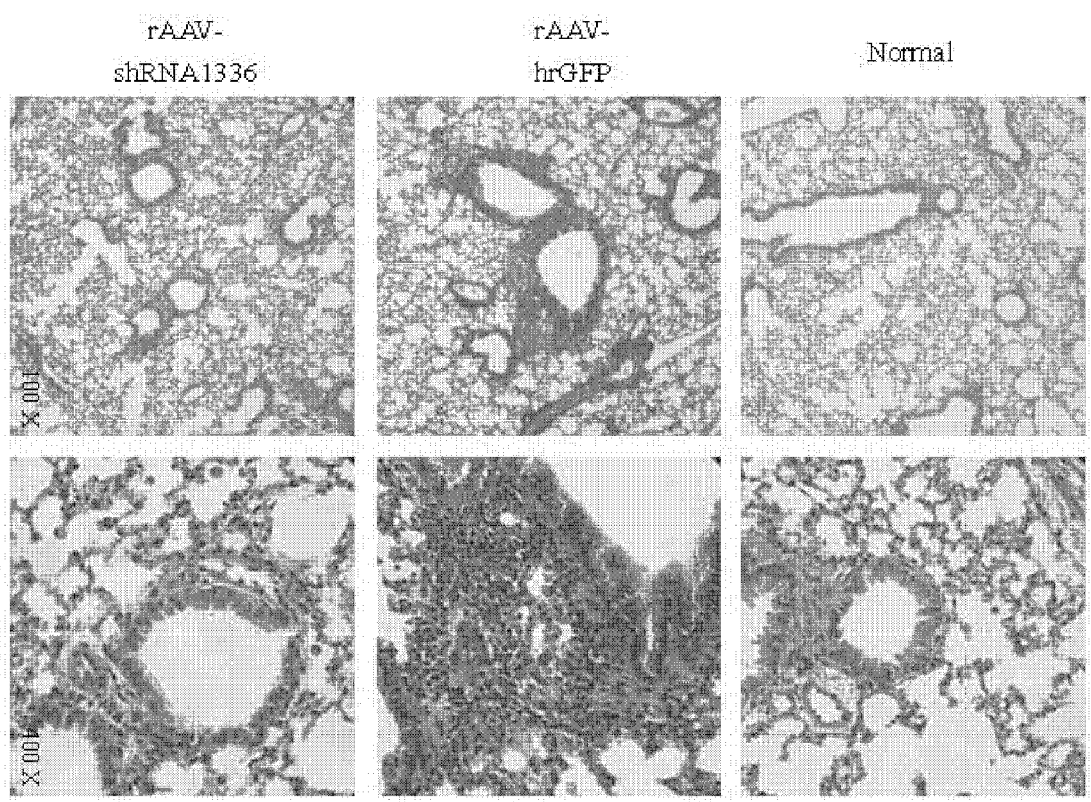
Figure 6A:
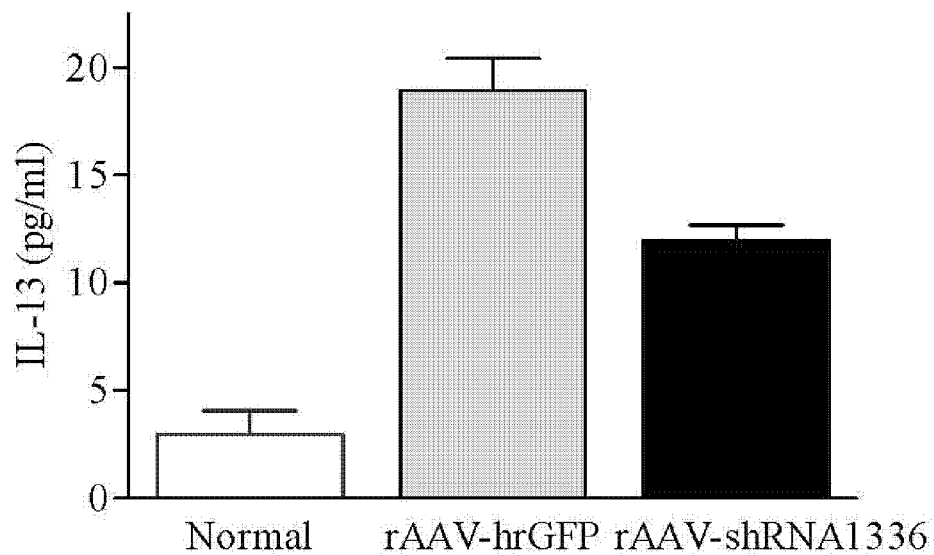
FIG. 6. Expression of cytokines and chemokines in rAAV-shRNA-treated mice. Panels (a) and (b) show levels of IL-13 and eotaxin measured by ELISA in BALF samples. Panel (c), RNA samples from lung tissues were analyzed for cytokine and chemokine gene expression by means of RT-PCR. Normal (n=3-7), sensitized (n=5-7), rAAV-GFP (n=6-10) and rAAV-sh1336 (n=6-11) were investigated (*p<0.05, nonparametric Mann-Whitney test).
Figure 6B:
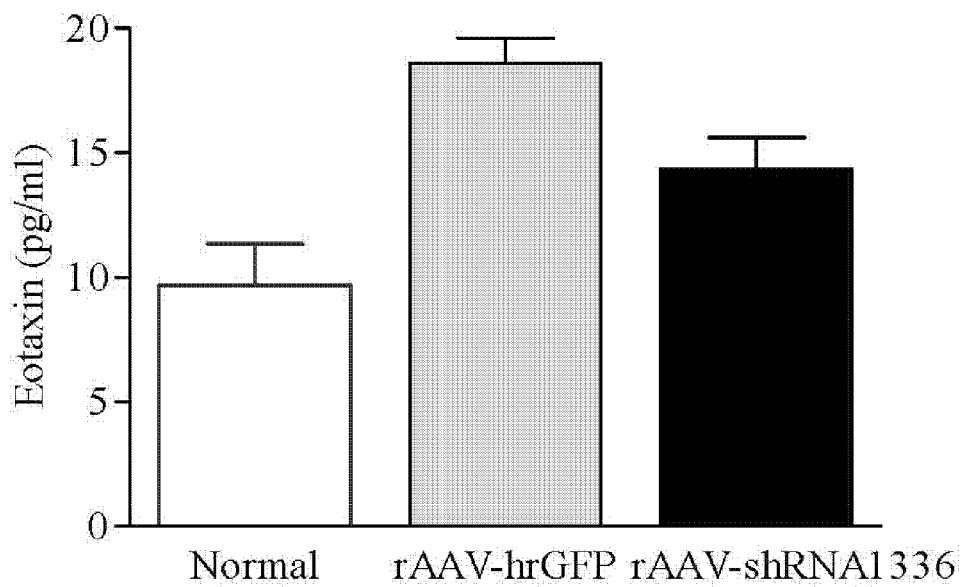
Figure 6C:
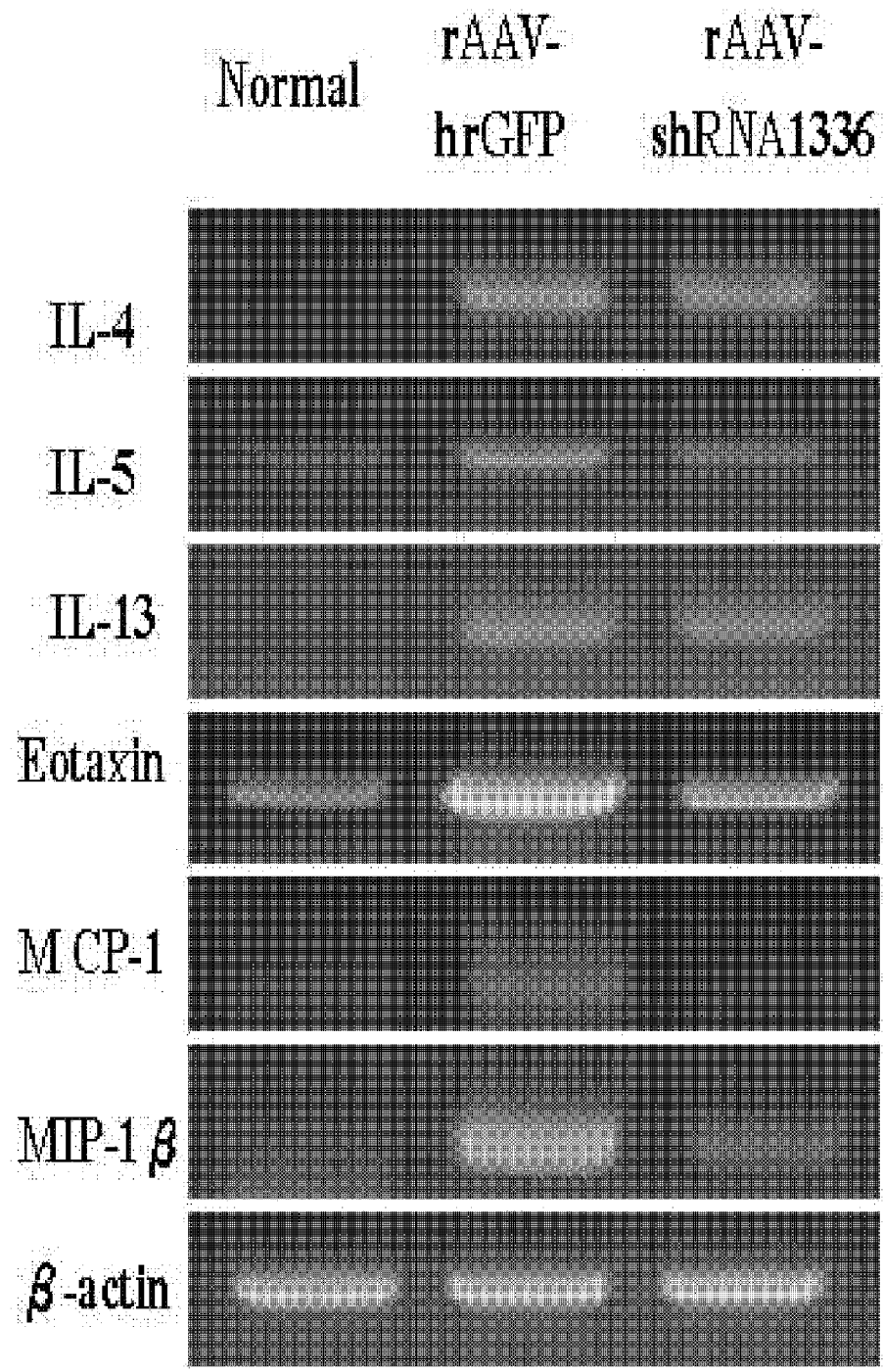

Treatment with rAAV-shRNA1336 resulted in a significant reduction in immunopathological allergic responses among OVA-sensitized mice. Firstly, OVA specific IgE serum level appeared to be significantly lower in asthmatic mice treated with rAAV-shRNA compared to animals treated with rAAV-GFP (FIG. 5a). Secondly, infection with rAAV-shRNA reduced eosinophil infiltration in BALF (FIG. 5b) as well as infiltration of inflammatory cells in the lung tissues of asthmatic mice (FIG. 5c). IL-13 was a cytokine whose expression has been associated with AMCase expression and eotaxin, an eosinophil specific chemo-attractant. Levels of IL-13 and eotaxin were measured in BALF cells using commercially available ELISA kits. As shown in FIGS. 6a and 6b, concentrations of IL-13 and eotaxin concentrations were lower in mice treated with normal saline only. In contrast, OVA-sensitized mice treated by rAAV-GFP had higher levels of IL-13 and eotaxin compared with OVA-sensitized mice receiving rAAV-shRNA. Altogether, these findings suggest that rAAV-shRNA can reduce levels of IL-13 and eotaxin. Other Th2-associated cytokines (IL-4 and IL-5) were also measured and inflammatory chemokines (MCP-1 and MIP-1β) in lung cells of mice receiving different rAAV treatments. RNA samples from lung tissues of mice receiving normal saline were used as negative controls. The main findings are depicted in FIG. 6c. Treatment with rAAV-shRNA resulted in a reduced expression of all cytokine and chemokine genes in the lung, although IL-4 and IL-13 inhibition was not as prominent as that observed with chemokines (eotaxin, MCP-1 and MIP-1β). A relatively reduced expression of IL-5 in the lung was also found.

What is claimed is:

1. An isolated small interfering RNA (siRNA) polynucleotide having the nucleotide sequence set forth in SEQ ID NO: 3.

2. A composition comprising: (a) an siRNA comprising SEQ ID NO:3, and (b) a carrier which is an Adeno-associated Vector (AAV) or other viral vector, wherein the siRNA is targeted to a transcript encoding a protein named acidic mammalian chitinase (AMCase) involved in airway hyper responsiveness and inflammation in mammals.

3. The composition of claim 2, wherein the carrier further comprises a liposome or liposome based transfection agent.

4. The composition of claim 2, wherein:
the siRNA has a core duplex region whose sense strand sequence consists of at least 17 consecutive nucleotides as set forth in any of the sequences presented in SEQ ID NO:3.

5. The composition of claim 2, wherein:
the siRNA has a core duplex region whose sense strand sequence consists of at least 15 consecutive nucleotides as set forth in any of the sequences presented in SEQ ID NO: 3.

* * * * *

SEQUENCE LISTING

```
<160> NUMBER OF SEQ ID NOS: 9

<210> SEQ ID NO 1
<211> LENGTH: 25
<212> TYPE: RNA
<213> ORGANISM: Artificial Sequence
<220> FEATURE:
<223> OTHER INFORMATION: siRNA for AMCase inhibition
<220> FEATURE:
<221> NAME/KEY: scRNA
<222> LOCATION: (1)..(25)
<220> FEATURE:
<221> NAME/KEY: scRNA
<222> LOCATION: (1)..(25)
<223> OTHER INFORMATION: siRNA 185

<400> SEQUENCE: 1
gcagaacaau gagaucacca ccaua                                          25

<210> SEQ ID NO 2
<211> LENGTH: 25
<212> TYPE: RNA
<213> ORGANISM: Artificial Sequence
<220> FEATURE:
<223> OTHER INFORMATION: siRNA for AMCase inhibition
<220> FEATURE:
```

```
<221> NAME/KEY: scRNA
<222> LOCATION: (1)..(25)
<220> FEATURE:
<221> NAME/KEY: scRNA
<222> LOCATION: (1)..(25)
<223> OTHER INFORMATION: siRNA 897

<400> SEQUENCE: 2
ggguucuggg ccuacuauga gauuu                                         25

<210> SEQ ID NO 3
<211> LENGTH: 25
<212> TYPE: RNA
<213> ORGANISM: Artificial Sequence
<220> FEATURE:
<223> OTHER INFORMATION: siRNA for AMCase inhibition
<220> FEATURE:
<221> NAME/KEY: scRNA
<222> LOCATION: (1)..(25)
<220> FEATURE:
<221> NAME/KEY: scRNA
<222> LOCATION: (1)..(25)
<223> OTHER INFORMATION: siRNA 1336

<400> SEQUENCE: 3
ggcagugcau caauggaauc acaua                                         25

<210> SEQ ID NO 4
<211> LENGTH: 29
<212> TYPE: DNA
<213> ORGANISM: Mus musculus
<220> FEATURE:
<221> NAME/KEY: primer_bind
<222> LOCATION: (1)..(29)

<400> SEQUENCE: 4
atcagaattc tatggccaag ctacttctc                                     29

<210> SEQ ID NO 5
<211> LENGTH: 32
<212> TYPE: DNA
<213> ORGANISM: Mus musculus
<220> FEATURE:
<221> NAME/KEY: primer_bind
<222> LOCATION: (1)..(32)

<400> SEQUENCE: 5
tttctgcggc cgcatggcat taggttcatg gc                                 32

<210> SEQ ID NO 6
<211> LENGTH: 21
<212> TYPE: DNA
<213> ORGANISM: Mus musculus
<220> FEATURE:
<221> NAME/KEY: primer_bind
<222> LOCATION: (1)..(21)

<400> SEQUENCE: 6
gaaactacat tcaattccat c                                             21

<210> SEQ ID NO 7
<211> LENGTH: 21
<212> TYPE: DNA
<213> ORGANISM: Mus musculus
<220> FEATURE:
<221> NAME/KEY: primer_bind
<222> LOCATION: (1)..(21)

<400> SEQUENCE: 7
```

```
ctagaagcac ttgcggtgca c                                              21

<210> SEQ ID NO 8
<211> LENGTH: 21
<212> TYPE: DNA
<213> ORGANISM: Mus musculus
<220> FEATURE:
<221> NAME/KEY: primer_bind
<222> LOCATION: (1)..(21)

<400> SEQUENCE: 8
atggtgagca agcagatcct g                                              21

<210> SEQ ID NO 9
<211> LENGTH: 21
<212> TYPE: DNA
<213> ORGANISM: Mus musculus
<220> FEATURE:
<221> NAME/KEY: primer_bind
<222> LOCATION: (1)..(21)

<400> SEQUENCE: 9
ggtgcgctcg tacacgaagc c                                              21
```